United States Patent [19]

Harris

[11] 4,449,935
[45] May 22, 1984

[54] TOOTH CROWN REMOVER

[75] Inventor: William H. Harris, Oklahoma City, Okla.

[73] Assignee: Hampton Research & Engineering, Inc., Oklahoma City, Okla.

[21] Appl. No.: 468,814

[22] Filed: Feb. 22, 1983

[51] Int. Cl.³ .............................................. A61C 3/08
[52] U.S. Cl. .................................................... 433/151
[58] Field of Search ............... 433/151, 150, 121, 118; 72/705

[56] References Cited

U.S. PATENT DOCUMENTS

| | | | |
|---|---|---|---|
| 571,176 | 11/1896 | Stockton | 433/151 |
| 2,776,490 | 1/1957 | Carfagni | 433/151 |
| 3,254,412 | 6/1966 | Armao | 433/151 |
| 3,686,756 | 8/1972 | Pankratz | 433/151 |

FOREIGN PATENT DOCUMENTS 2743067  3/1979  Fed. Rep. of Germany ...... 433/150

Primary Examiner—John J. Wilson
Attorney, Agent, or Firm—Robert K. Rhea

[57] ABSTRACT

An elongated mandrel is coaxially secured at one end to one end of a larger diameter handle. The other end portion of the mandrel converges and terminates in an annular outstanding shoulder facing the handle. A sleeve-like hammer slidably surrounds the mandrel and is spring urged for impacting on the adjacent handle end when manually moved away from the handle and released. The hammer is provided with an outstanding flange adjacent the handle for manually moving the hammer away from the handle.

2 Claims, 1 Drawing Figure

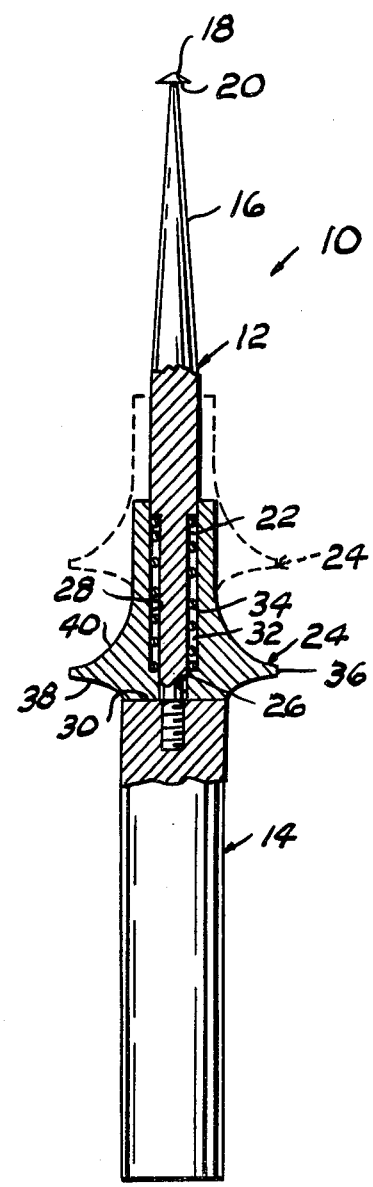

TOOTH CROWN REMOVER

BACKGROUND OF THE INVENTION

1. Field of the Invention

The present invention relates to dental tools and more particularly to a tooth crown remover.

It is sometimes necessary to remove a crown from a tooth in order to remove decayed portions of the tooth and replace the crown. Since the crown in place fits and completes the contour of the tooth, the old crown is usually difficult to remove.

This invention provides a hand held tool which will engage the edge of the crown overlapping the tooth and effectively remove it from the tooth.

2. Description of the Prior Art

I do not know of any patents disclosing a tooth crown remover.

SUMMARY OF THE INVENTION

An elongated mandrel is diametrically reduced at one end portion and coaxially secured to one end of a larger diameter handle. The end portion of the mandrel, opposite the handle, converges toward its free end and terminates in a small diameter head defining a thin edge annular lip or shoulder facing the handle and perpendicular to the longitudinal axis of the mandrel. A centrally bored and counterbored hammer slidably surrounds the end portion of the mandrel connected with the handle and defines an annular space around the diametrically reduced end portion of the mandrel which receives a helical spring normally urging the hammer toward the handle. The hammer is characterized by a diametrically enlarged annular outstanding flange adjacent its end facing the handle. The end surface of the handle connected with the mandrel forms an anvil against which the adjacent end of the hammer impacts when the user, by grasping the handle, moves the hammer toward the free end of the mandrel with his thumb and releases it.

The principal object of this invention is to provide a hand tool for removing a crown from a tooth.

BRIEF DESCRIPTION OF THE DRAWING

The single FIGURE is a vertical cross sectional view, partially in elevation, illustrating hammer movement by dotted lines.

DESCRIPTION OF THE PREFERRED EMBODIMENT

Like characters of reference designate like parts in those figures of the drawings in which they occur.

In the drawings:

The reference numeral 10 indicates the tool, as a whole, which is elongated cylindrical in general configuration and symetrical about its longitudinal axis. The tool comprises an elongated mandrel 12 coaxially secured to a larger diameter elongated handle 14. The other end portion of the mandrel 12 is tapered, as at 16, to converge toward a substantially conical-shaped head end 18 having a selected base diameter less than the diameter of the mandrel forming an annular shoulder 20 terminating at its perimeter in a hairline edge. The plane of the shoulder 20 is perpendicular to the longitudinal axis of the mandrel. The end portion of the mandrel, adjacent its connection with the handle, is diametrically reduced, as at 22, for the purpose presently explained.

A generally cylindrical sleeve-like hammer 24 coaxially surrounds the end portion of the mandrel adjacent the handle. The bore 26 of the hammer slidably surrounds the diametrically reduced portion 22 of the mandrel. The hammer is counterbored from its end opposite the handle, as at 28, on a diameter slidably surrounding the mandrel. The length of the hammer is such that it extends from the hammer end 30 longitudinally toward the head end of the mandrel beyond the mandrel diametrically reduced portion 22 thus forming an annular space 32. The space 32 receives a helical spring 34 normally urging the hammer toward the handle end surface 30. The hammer 24 is further characterized by a diametrically enlarged flange 36 at its end portion adjacent the handle characterized by opposing arcuate surfaces 38 and 40 converging outwardly toward the perimeter of the flange.

OPERATION

In operation, the dentist manually grasps the handle 14 with his fingers surrounding the handle and the end of his thumb adjacent the flange surface 38. The mandrel head lip or shoulder 20 is positioned to engage the edge of a tooth crown, not shown, projecting toward the gum of a patient and while holding the shoulder 20 in this position the hammer is manually forced in an axial sliding direction along the mandrel toward its head end wherein the dentist slides his thumb outwardly off the arcuate flange surface 38 to release the hammer which, by the resilience of the spring, is forced toward and impacts against the handle anvil surface 30 thus imparting a longitudinal jerk or axial movement of the device to loosen and/or remove the tooth crown.

Obviously the invention is susceptible to changes or alterations without defeating its practicability. Therefore, I do not wish to be confined to the preferred embodiment shown in the drawings and described herein.

I claim:

1. A tooth crown remover, comprising:
    an elongated handle having an end surface forming an anvil;
    a mandrel coaxially secured to the anvil end of said handle,
        the end portion of said mandrel opposite the handle coaxially converges away from the handle and terminates in an annular shoulder facing the handle normal to the mandrel axis;
    a sleeve-like hammer longitudinally slidably surrounding the end portion of said mandrel adjacent said handle; and,
    spring means interposed between said hammer and said mandrel for biasing said hammer toward said handle,
        the end portion of said mandrel adjacent said handle being diametrically reduced to form an annular space for nesting said spring means.
2. The tooth crown remover according to claim 1 in which said hammer is provided with an annular outstanding flange adjacent said handle.

* * * * *